United States Patent
Alewelt et al.

(10) Patent No.: US 6,548,691 B2
(45) Date of Patent: Apr. 15, 2003

(54) PROCESS FOR PRODUCING CARBONIC ACID DIARYL ESTER

(75) Inventors: Wolfgang Alewelt, Krefeld (DE); Steffen Kühling, Meerbusch (DE)

(73) Assignee: Bayer Aktiengesellscaft, Leverkusen (DE)

( * ) Notice: Subject to any disclaimer, the term of this patent is extended or adjusted under 35 U.S.C. 154(b) by 0 days.

(21) Appl. No.: 10/015,311

(22) Filed: Dec. 12, 2001

(65) Prior Publication Data

US 2002/0077446 A1 Jun. 20, 2002

(30) Foreign Application Priority Data

Dec. 19, 2000 (DE) .......................................... 100 63 296

(51) Int. Cl.$^7$ ............................................... C07C 69/96
(52) U.S. Cl. ...................................................... 558/274
(58) Field of Search ......................................... 558/274

(56) References Cited

U.S. PATENT DOCUMENTS 4,016,190 A  4/1977  Böckmann et al. ......... 260/463
5,155,205 A  * 10/1992 Ebert et al.

FOREIGN PATENT DOCUMENTS

JP  11005766 A  * 1/1999

OTHER PUBLICATIONS

Brunelle, Tetrahedron Letters, Novel Catalysis of o–Nitrophenyl Carbonates by p–Dimethylaminopyridine, 23(17), pp. 1739–1742.*

Chemistry and Physics, Polymer Reviews, , H. Schnell, vol. 9, John Wiley & Sons (Month Unavailable) 1964, pp. 44–57 (See pp. 50/51) Chemistry and Physics of Polycarbonates.

* cited by examiner

Primary Examiner—Johann Richter
Assistant Examiner—Paul A. Zucker
(74) Attorney, Agent, or Firm—Joseph C. Gil; James R. Franks

(57) ABSTRACT

An improvement to the interfacial boundary process for producing carbonic acid diaryl esters is disclosed. In the two-stage process that entails phosgene and monophenols reaction in an inert solvent, in the presence of alkali and in the presence of a nitrogen base catalyst, the improvement comprising maintaining a temperature below 50° C. in the first and second stages.

6 Claims, No Drawings

PROCESS FOR PRODUCING CARBONIC ACID DIARYL ESTER

CROSS REFERENCE TO RELATED PATENT APPLICATION

The present patent application claims the right of priority under 35 U.S.C. §119 (a)–(d) of German Patent Application No. 100 63 296.3, filed Dec. 19, 2000.

FIELD OF THE INVENTION

The present invention relates to a process for producing carbonic acid diaryl esters by reacting monophenols and phosgene in an inert solvent in the presence of alkali and a nitrogen base in an interfacial process at low reaction temperatures.

SUMMARY OF THE INVENTION

An improvement to the interfacial boundary process for producing carbonic acid diaryl esters is disclosed. In the two-stage process that entails phosgene and monophenols reaction in an inert solvent, in the presence of alkali and in the presence of a nitrogen base catalyst, the improvement comprising maintaining a temperature below 50° C. in the first and second stages.

BACKGROUND OF THE INVENTION

The production of carbonic acid diaryl esters by the phase interface process is basically known from the literature, cf. Chemistry and Physics of Polycarbonates, Polymer Reviews, H. Schnell, Vol. 9, John Wiley and Sons, Inc. (1964), p. 50/51). U.S. Pat. No. 4,016,190 describes a process for the production of carbonic acid diaryl esters which is carried out at temperatures >65° C. and in which nitrogen bases are used as catalysts.

Aryldialkyl urethanes are typically formed as secondary products when carrying out these processes, either due to the reaction of phosgene with the tertiary amines used as catalysts to form carbamic acid chloride and subsequent reaction with the phenol present to form the urethane (1) or due to the reaction of aryl chlorocarbonic acid ester from phenol and phosgene with the tertiary amines (2) in accordance with the following general reaction scheme:

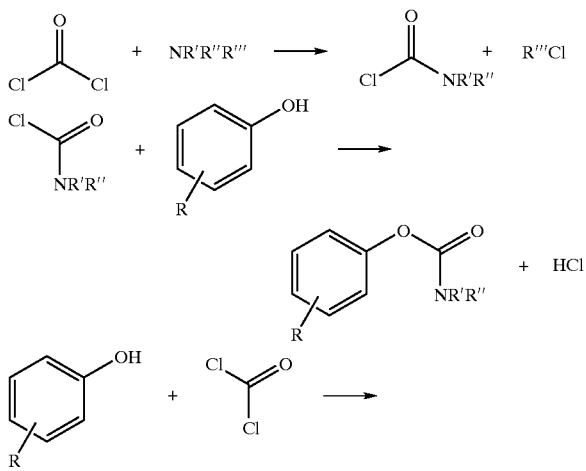

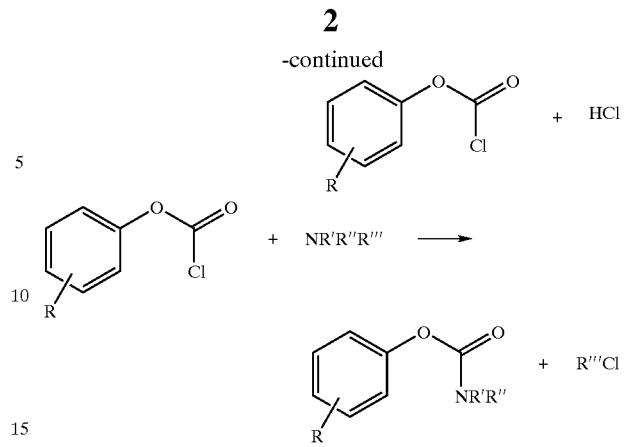

wherein R represents the radicals according to formula (I) (see below) and R', R" and R'" generally represent organic radicals.

These compounds interfere with the melt transesterification process to the polycarbonate and are concentrated, in particular, in a carbonic acid diphenyl ester cycle. It is therefore particularly important to suppress the formation of these Aryldialkyl urethanes and to remove them from the carbonic acid diaryl ester.

However, the processes known from the state of the art, based on monophenols and phosgene in a solvent and using a nitrogen base as catalyst are not satisfactory with respect to the purity of the products obtained, in particular with respect to the chlorine and urethane content thereof. For this reason, the products obtainable by these processes additionally have to be subjected to further purification processes.

DETAILED DESCRIPTION OF THE INVENTION

Starting from the state of the art, the object was accordingly to provide a process for producing carbonic acid diaryl esters which are depleted in chlorine and, in particular, in secondary products, especially in urethane.

It has now surprisingly been found that, when producing carbonic acid diaryl esters by reaction of monophenols and phosgene in an inert solvent by the phase interface process in the presence of alkali while using nitrogen based catalysis, low reaction temperatures are required for obtaining high product purity in the carbonic acid diaryl ester and for avoiding the aforementioned secondary reactions.

The catalysts to be used in the process according to the invention are tertiary amines, N-alkyl piperidines or onium salts. Tributyl amine, triethyl amine and N-ethylpiperidine are preferably used. N-ethylpiperidine is quite particularly preferred. The concentrations of the catalysts are 0.0001 mol % to 0.1 mol %, preferably 0.01 mol % to 0.075 mol %, based on the phenol used.

The suitable alkali include lye (Na, K, Li, Ca-hydroxide), preferably sodium hydroxide solution, and is preferably used as a 20 to 55 wt. %, particularly preferably 30 to 50 wt. % solution in the process according to the invention.

Phosgene may be used in liquid or gaseous form or dissolved in the inert solvent.

Suitable monophenols for use in the process according to the invention include phenols of formula (I)

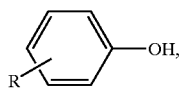

wherein
R is hydrogen, tert.-butyl, halogens or a branched or unbranched $C_8$ and/or $C_9$ alkyl radical, therefore phenol itself, alkylphenols such as cresols, p-tert.-butylphenol, p-cumylphenol, p-n-octylphenol, p-iso-octylphenol, p-n-nonylphenol and p-iso-nonylphenol, halogen phenols such as p-chlorophenol, 2,4-dichlorophenol, p-bromophenol and 2,4,6-tribromophenol may be used. Phenol is preferred.

Inert organic solvents, for example dichloromethane, toluene, the various dichloroethanes and chloropropane compounds, chlorobenzene and chlorotoluene may be used in the process according to the invention, dichloromethane preferably being used.

The reaction may be conducted both discontinuously (batchwise) and continuously, preferably continuously, and is preferably carried out in a plug flow without significant back-mixing. This may be effected, for example, in tubular reactors. The two phases (aqueous and organic phase) may be thoroughly mixed by diaphragm fittings, static mixers and/or pumps.

The reaction initiated by combining the phosgene, the inert solvent, which preferably serves only as solvent for the phosgene, and the phenol, which has preferably already been dissolved in the lye beforehand. Generally, the pH of the first stage in the process according to the invention is preferably adjusted by the ratio of lye/phenol/phosgene in such a way that the pH lies in the range of 11.0 to 12.0, preferably 11.2 to 11.8. The reaction temperature is kept at <50° C., preferably <40° C., quite particularly preferably <35° C. by cooling. The residence time lies in the range of 2 seconds to 300 seconds, preferably in the range of 4 seconds to 200 seconds in the first stage in the case of the continuously conducted process according to the invention.

The reaction is completed to form the carbonic acid diaryl ester in the second stage of the process according to the invention. The catalyst is preferably provided at this stage. The reaction mixture is cooled in the process according to the invention directly after or during addition of the catalyst. The reaction temperature is kept at <50°, preferably <40° C., quite particularly preferably <35° C. by cooling. It may be advantageous to add the catalyst at a plurality of, preferably two, points of the second stage of the process.

The chloroformic acid aryl ester content in the resultant carbonic acid diaryl ester is <2 ppm, preferably <0.5 ppm in the process according to the invention.

An arylpiperidyl urethane content in the resultant carbonic acid diaryl ester of <100 ppm, preferably <75 ppm, quite particularly preferably <50 ppm is obtained by the process according to the invention.

The pH is preferably regulated in the second stage of the process according to the invention by measuring the pH (which is preferably measured online in the continuous process) and corresponding adjustment of the pH by addition of the lye. The quantity of lye supplied is adjusted in such a way that the pH in the second stage of the process lies in the range of 7.5 to 10.5, preferably 8 to 9.

In the process according to the invention, phosgene is supplied in a ratio of 1.01 to 1.15 mol %, preferably 1.05 to 1.12 mol %, based on the phenol. The solvent is added in such a way that the carbonic acid diphenyl ester exists in a 5 to 60% solution, preferably 20 to 45% solution after the reaction.

After the reaction, the organic phase containing the carbonic acid diaryl ester is usually washed with an aqueous liquid and separated as far as possible from the aqueous phase after each washing procedure. Washing is preferably carried out with de-ionized water. The carbonic acid diaryl ester solution is usually cloudy after washing and separation of the washing liquid. Aqueous liquids, for example dilute mineral acids such as HCl or $H_3PO_4$ are used to separate the catalyst and water which is completely de-ionized is used for further purification. The concentration of HCl or $H_3PO_4$ in the washing liquid may be, for example, 0.5 to 1.0 wt. %. The organic phase is preferably washed twice by way of example.

Basically known separating vessels, phase separators, centrifuges or coalescers or also combinations of these devices may be used as phase-separating devices for separating the washing liquid from the organic phase.

The solvent is evaporated to obtain the high-purity carbonic acid diaryl ester. Evaporation may be carried out in a plurality of evaporator stages. For example, it is carried out through one or more successive distillation columns in which the solvent is separated from the carbonic acid diaryl ester.

This purification stage or stages may be conducted, for example, continuously in such a way that the sump temperature during distillation is >150° C. to 310° C., preferably >160 to 230° C. The pressures required to carry out these distillation processes are between 1 and 1000 mbar, preferably between 5 and 100 mbar.

The resultant carbonic acid diesters are distinguished by very high purity with GC purities (cool on column method) >99.99%, preferably 99.9925%, quite particularly preferably >99.995% and extremely good transesterification behaviour, so a polycarbonate of excellent quality may be produced therefrom.

The production of aromatic oligo/polycarbonates by the melt transesterification process is known from the literature and has already been described, for example, in the Encyclopedia of Polymer Science, Vol. 10 (1969), Chemistry and Physics of Polycarbonates, Polymer Reviews, H. Schnell, Vol 9, John Wiley and Sons, Inc. (1964) or U.S. Pat. No. 5,340,905.

EXAMPLES

Example 1

A mixture of 117 kg/h completely de-ionized water with 48 kg/h 50% NaOH and 54.9 kg/h phenol is continuously combined with a solution of 98 kg/h methylene chloride and 31.2 kg/h phosgene (8 mol % excess, based on phenol) in a cooled tubular reactor. After an average residence time of 15 seconds, 6.5 kg/h 50% NaOH are accordingly added to this reaction mixture in the second stage of the process and 1.1 kg/h (0.9% in methylene chloride) of the catalyst N-ethylpiperidine are added directly afterwards and the reaction mixture immediately cooled to 30° C. The reaction mixture is then mixed constantly by conveyance through a pipe provided with constrictions. The organic phase is subsequently separated from the aqueous phase. After washing 0.6% HCl and water and final phase separation, a 99.996% (GC method, cool on column method) diphenylcarbonate is obtained after evaporation of the methylene chloride. The phenylpiperidyl urethane content is 40 ppm and the chloroformic acid phenyl ester content is <0.5 ppm.

Comparison Example 1

As example 1, but the reaction temperature is not cooled after addition of the catalyst so the temperature is 55° C.

After washing with 0.6% HCl and water and final phase separation, a 99.97% (GC method, cool on column method) diphenylcarbonate is obtained after evaporation or the methylene chloride. The phenylpiperidyl urethane content is 300 ppm and the chloroformic acid phenyl ester content is <0.1 ppm.

Example 2

As example 1, but 0.55 kg/h N-ethylpiperidine (0.9% in methylene chloride) are added after 15 seconds, the reaction solution immediately cools to 30° C. and a further 0.55 kg/h N-ethylpiperidine (0.9% in methylene chloride) added after a residence time of 1 minute, once the reaction mixture has been mixed constantly by conveyance through a pipe provided with constrictions. The mixture is subsequently cooled to 30° C. again. The organic phase is then separated from the aqueous phase. After washing with 0.6% HCl and water and final phase separation, a 99.998% (GC method, cool on column method) diphenylcarbonate is obtained after evaporation of the methylene chloride. The phenylpiperidyl urethane content is 20 ppm and the chloroformic acid phenyl ester content is <0.5 ppm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In the interfacial boundary process for producing carbonic acid diaryl esters from phosgene and monophenols in an inert organic solvent, in the presence of an alkaline solution and a nitrogen base catalyst, the process including:
   (i) a first stage wherein phosgene, said inert organic solvent and phenol in solution are combined to form a material system having a pH of 11.0 to 12.0; and
   (ii) a second stage wherein the reaction to form carbonic acid diaryt ester is completed,
the improvement comprising maintaining a temperature below 50° C. in each of said first and second stages, and wherein the carbonic acid diaryl esters have a urethane content of less than 100 ppm.

2. The process of claim 1 wherein the temperature in each of said first and second stages is below 40° C.

3. The process of claim 1 wherein the temperature in each of said first and second stages is below 35° C.

4. The process according to claim 1 further comprising converting the carbonic acid diaryl ester to a polycarbonate through a transesterification reaction.

5. The process of claim 1 wherein said nitrogen base is ethylpiperidine.

6. The process of claim 1 wherein said inert organic solvent is selected from dichloromethane, toluene, chlorobenzene and chlorotoluene.

* * * * *